(12) United States Patent
Zhou et al.

(10) Patent No.: US 11,029,285 B2
(45) Date of Patent: Jun. 8, 2021

(54) REAL-TIME AND QUANTITATIVE MEASUREMENT METHOD FOR CELL TRACTION FORCE

(71) Applicant: HUNAN AGRICULTURAL UNIVERSITY, Changsha (CN)

(72) Inventors: Tiean Zhou, Changsha (CN); Lun Xiong, Changsha (CN); Zhen Zhou, Changsha (CN); Jingyuan Huang, Changsha (CN); Haibo Shen, Changsha (CN); Dongqin Bao, Changsha (CN); Fushen Huang, Changsha (CN); Kebin Wu, Changsha (CN); Weisong Pan, Changsha (CN); Jia Zhao, Changsha (CN); Bin Hong, Changsha (CN)

(73) Assignee: HUNAN AGRICULTURAL UNIVERSITY, Changsha (CN)

( * ) Notice: Subject to any disclaimer, the term of this patent is extended or adjusted under 35 U.S.C. 154(b) by 189 days.

(21) Appl. No.: 16/336,883

(22) PCT Filed: Aug. 28, 2017

(86) PCT No.: PCT/CN2017/099247
§ 371 (c)(1),
(2) Date: Mar. 26, 2019

(87) PCT Pub. No.: WO2018/041060
PCT Pub. Date: Mar. 8, 2018

(65) Prior Publication Data
US 2019/0317050 A1    Oct. 17, 2019

(30) Foreign Application Priority Data
Aug. 29, 2016 (CN) .......................... 201610755868.1

(51) Int. Cl.
G01N 29/12 (2006.01)
C12N 5/04 (2006.01)
(Continued)

(52) U.S. Cl.
CPC ............... *G01N 29/12* (2013.01); *C12N 5/04* (2013.01); *C12N 5/06* (2013.01); *G01N 29/2443* (2013.01);
(Continued)

(58) Field of Classification Search
CPC ............... G01N 29/12; G01N 29/2443; G01N 33/4833; G01N 2291/02827; G01N 29/036; G01N 29/022
See application file for complete search history.

(56) References Cited

U.S. PATENT DOCUMENTS

2004/0235198 A1    11/2004  Marx et al.

FOREIGN PATENT DOCUMENTS

| CN | 1283270 A | 11/1998 |
|---|---|---|
| CN | 104232480 A | 12/2014 |
| CN | 106404915 | 2/2017 |

OTHER PUBLICATIONS

Search Report of PCT/CN2017/099247, dated Year: 2017.
(Continued)

*Primary Examiner* — David Z Huang
(74) *Attorney, Agent, or Firm* — Dragon Sun Law Firm, PC; Jinggao Li, Esq.

(57) ABSTRACT

A real time and quantitative method of measuring traction force of living cells include the following procedures. Place AT-cut and BT-cut quartz crystals of the same frequency, surface morphology and/or modified with the same cell adhesion molecules in petri dishes or detection cells; add the cells to the petri dishes or detection cells, the cell traction force at arbitrary time t during adhesion of the cells or under
(Continued)

different internal/external environmental stimulations is estimated by the following equation: $\Delta S_t = (K_{AT} - K_{BT})^{-1} [t_q^{AT} \Delta f_t^{AT}/fr^{AT} - tq^{BT} \Delta f_t^{BT}/fr^{BT}]$. The method can be used to track the dynamic changes of cells generated force during the adhesion of cells and under different internal/external environmental stimulations, such as the effects of drugs. The drugs can be added before or after the adhesion of the cells. This method is suitable for all adherent cells, including primary cells and passage cells.

4 Claims, 9 Drawing Sheets

(51) Int. Cl.
　　*C12N 5/07*　　　(2010.01)
　　*G01N 29/24*　　　(2006.01)
　　*G01N 33/483*　　　(2006.01)
(52) U.S. Cl.
　　CPC .............. *G01N 33/4833* (2013.01); *G01N 2291/02827* (2013.01)

(56) References Cited

OTHER PUBLICATIONS

Written opinion of PCT/CN2017/099247, dated Year: 2017.
RO 101 of PCT/CN2017/099247, Year: 2017.
First office action of Chinese patent application CN201610755868.1, dated Year: 2018.
Zhou, Tiean et al. Real-time monitoring of contractile properties of H9C2 car-diomyoblasts by using a quartz crystal microbalance. Analytical Methods. Dec. 2, 2015 (Dec. 2, 2015), 8(3), ISSN: 1759-9660.
Khalili, Amelia Ahmad et al. A Review of Cell Adhesion Studies for Biomedical and Biological Applications. International Journal of Molecular Sciences. Aug. 5, 2015 (Aug. 5, 2015), 16(8), ISSN: 1422-0067.
Tan, Liang et al. Dynamic measurement of the surface stress induced by the attachment and growth of cells on Au electrode with a quartz crystal micro balance. Biosensors and Bioelectronics. Aug. 22, 2008 (Aug. 22, 2008), vol. 24, ISSN: 0956-5663.
Cheek, Graham T. et al. Measurement of hydrogen uptake by palladium using a quartz crystal microbalance. J. Electroanal. Chem. Jan. 10, 1990 (Jan. 10, 1990), vol. 277, ISSN: 0022-0728, p. 342, pp. 345 and 346.

REAL-TIME AND QUANTITATIVE MEASUREMENT METHOD FOR CELL TRACTION FORCE

CROSS-REFERENCE TO RELATED APPLICATIONS

This application is a national stage application of PCT Application No. PCT/CN2017/099247. This applications claims priority from PCT Application No. PCT/CN2017/099247, filed Aug. 28, 2017, and CN Application No. 201610327604.6, filed Aug. 29, 2016, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE PRESENT DISCLOSURE

The present disclosure relates to a real-time and quantitative measurement method for cell traction force.

BACKGROUND OF THE PRESENT DISCLOSURE

More and more studies have shown that cells communicate with each other and cells communicate with their microenvironment through force signals besides biochemical signals. The geometric and mechanical properties of the cellular microenvironment have a great impact on the morphology and function of the cells. Many physiological processes, including cell adhesion, cytoskeletal polarity, cell proliferation, cell differentiation, embryogenesis and development, cancer metastasis, wound healing, etc., are significantly affected by the transmission and sensing of physical forces between the cells and their microenvironments. The mechanical properties of cells are directly related to the composition and structure of cytoskeletons. The cytoskeleton is coupled to the extracellular matrix and adjacent cells by focal adhesion complex, cadherin, etc. respectively. The main cellular structures involved in cell force transduction include a cell membrane and a rigid cell cortex (consisting of actin, myosin and related proteins) closely connected to the cell membrane. The cortex is connected to the extracellular matrix by integrin, and forms focal adhesions with the extracellular matrix as the cell is gradually spread. The cytoplasmic actomyosin network is connected with the nucleus to apply contraction or traction force to the extracellular matrix (FIG. 1). Cell adhesion, the magnitude of cell traction force and the structure of the focal adhesions are related to the network structure of intracellular actin, molecular motor (e.g., myosin) and actomyosin, i.e., stress fibers.

Therefore, the contraction force of the cellular myosin or the cell traction force applied to its environment is an extremely important biophysical parameter in the field of cell biology and the like, and also has become a novel main target for the treatment of different diseases. Over the past few decades, several important technologies have been developed for assessing the cell traction force, and most of the technologies are limited to the calculation of traction force of a single, separate cell. The common feature of these technologies is the use of a soft elastic substrate to determine or calculate the cell traction force by the deformation of the substrate caused by the interaction of the cells with the elastic substrate. The elastic substrate is in two forms of a continuous substrate and a discontinuous substrate, the former includes a wrinkled thin silicone film and fluorescent microbeads embedded in a polyacrylamide gel, and the latter includes a micro-machined cantilever array and a micropillar array. Taking the micropillar array as an example, cells mainly adhere to micropillars perpendicular to the substrate, and the magnitude and direction of the traction force of a cell applying to the contact point can be directly determined according to the degree and direction of bending deformation of the micropillar. The micro-fabricated substrate is relatively complicated to fabricate; and because the cells and the substrate are in incomplete contact, and the morphology of the microstructure may affect the morphology and function of the adherent cells significantly, it is clear that this technology can only measure the cell traction force of these discontinuous, predetermined contact points.

The most widely used technology for cell traction force measurement so far is cell traction force microscopy (TFM) based on a continuous elastic substrate. The contact between the substrate and the cell is surface contact, closer to the true physiological environment of the cell, so the TFM for measuring the cell traction force is also more easily accepted by vast researchers. Since 1995, Lee, Jacobsen, Dembo et al. and other groups have developed several traction force microscopy technologies for measuring the cell traction force produced by migrating or resting cells on soft matrices. TFM calculates the cell traction force through the substrate deformation of cells cultured on a known elastic soft substrate, e.g., on a polyacrylamide (PA) gel. The cells are cultured on the elastic substrate, the traction force generated on the substrate during the cell spreading process causes the substrate to deform, and the deformation is reflected in the motion of fluorescent microbeads; the motion information of the fluorescent microbeads is acquired by a fluorescence microscopy, the strain information of the substrate is obtained after image processing, and then the traction force of the cells is quantitatively inverted through a certain mechanical model; the force distribution at various moments during cell contraction or migration can be visualized on a computer screen, so this method is also vividly referred to as Traction Force Microscopy (TFM).

From the quantitative theory, the measurement and calculation of the cell traction force fall into the scope of inverse problems, and a common important characteristic of the inverse problems is their mathematically ill state, causing the theoretical analysis or the numerical calculation to be specifically difficult, mainly reflecting in that the solution of an equation does not depend continuously on the observed data (input data). In other words, small deviations in the observed data can cause large changes in the solution. In practical problems, the error (or noise) of the observed data is generally inevitable. Therefore, the solution of the equation obtained by reversing the observed data with more or less error (or noise) is likely to deviate from the true solution.

In summary, most of the current methods for measuring the cell traction force are limited to single cell analysis. The soft substrate microfabrication process is complicated. In addition, the gaps between the micropillars are large, and the cells can only form adhesion structures with the pillars, which is different from the in vivo cell environment, so the structure and morphology of the micropillars may affect the normal physiology and function of the cells. The soft gel traction force microscopy is not a direct measurement on the traction force, but the traction force is calculated by observing the displacement of fluorescent labeled microbeads embedded in the gel using a fluorescence microscopy. Although the inversion step in the fabrication of a fluorescent film can ensure that most of fluorescent particles are deposited on the surface of the gel film, after 24 hours or 48 hours of immersion, the fluorescent particles may escape from pores into the medium and may fall to the film, causing a decrease in the fluorescence density on the surface of the fluorescent film. In the actual shooting process, a film plane that is 1 μm away from the surface is generally selected, but fluorescent particles of different planes may be captured at a relatively large depth of field of a common fluorescence microscopy, which brings errors to subsequent displacement calculations. Long-term laser irradiation can quench the fluorescein, and may also affect the cell viability. In addition, the elastic modulus of the gel film itself changes during the long-term immersion in the medium, so an accurate cell traction force must be obtained by measuring the elastic modulus of the gel film immersed in the medium at the corresponding time point. Therefore, the current methods for measuring the cell traction force are not suitable for long-term and continuous measurement of the cell traction force, and the changes in cell functions (e.g., cell growth and differentiation) take several days to several weeks. Obviously, the current cell traction force measurement technologies are not conducive to cell function researches, and therefore it is difficult to reflect the true physiological status of the cells.

The methods including the cell traction microscopy are limited to single cell measurement, the cells are heterogeneous, and a large amount of samples need to be analyzed for comparing and obtaining the statistically significant change characteristics in the cell traction force of cells under different pathologies or physiologies or different stimulations, so a lot of time is required. These technologies are all based on the deformation of the flexible substrate or sensor caused by cell force, where the cell traction force must be obtained by photography, lengthy image processing, model building and calculation. Therefore, the cell traction force microscopy is merely used at present in very limited specialized research laboratories (primarily in the field of mechanobiology).

Whatever it is gel used by the cell traction force microscopy or micro-fabricated soft micropillars, the cells can move freely on the substrate to have any shape, and the cell generated force cannot be automatically measured due to the lack of geometric constraints, so the cell traction force microscopy is not suitable for large-scale experiments. The micro-pattern technology can be used to immobilize individual cells, reduce the difference between the cells, and control the location of the cell generated force to simplify the calculation of the force, thereby increasing the throughput of cell traction force measurement. However, the micro-patterns increase the experimental steps and difficulty, and the measurement of force still needs to be obtained from the displacement data of fluorescent microbeads through complicated calculation. In addition, although the shape of the cells is controlled, the cells generated forces are still discretely distributed, so the deformation of the substrate caused by the cells is complicated and different among different cells.

In recent years, the cell force microscopy has been extended to the measurement of several cells and cell monolayer traction (monolayer traction microscopy (MTM)). Recent advances include 96-channel cell monolayer traction microscopy and Fourier transform 96-channel cell monolayer traction microscopy for the establishment of drug screening methods (the latter known as contraction force screening), based on cell monolayers and relative changes in the traction force after dosing 1 hour or several time points, so only the fixed end point is tested, but the continuous dynamic traction changes of cell adhesion and drug action are not tracked. Although these methods are very useful, it is more desirable to be able to achieve real-time, continuous and quantitative measurement of cell traction or contraction force generated by different numbers of cells or cells with different cell-cell interactions in a universal cell culture dish. Only in this way can the cell traction force be used as an important biophysical indicator to characterize the phenotype of cells, so as to better understand the cellular and molecular mechanisms of many important biological processes and be widely accepted and used in the biological fields including cell biology.

SUMMARY OF THE PRESENT DISCLOSURE

The conventional methods for measuring the cell traction force rely primarily on cell-induced soft substrate deformation, which is measured or tracked by an optical or fluorescence microscopy. The present disclosure is intended to overcome the deficiencies of the prior arts and provide a real-time and quantitative measurement method for cell traction force.

In order to achieve the above objective, the technical solution provided by the present disclosure is:

The real-time and quantitative measurement method for cell traction force includes the following steps:

(1) placing an AT-cut quartz crystal and a BT-cut quartz crystal in culture dishes or detection cells; the AT-cut quartz crystal has the same frequency, surface morphology and/or modified surface adhesion molecules as the BT-cut quartz crystal; and (2) adding cells to be tested to the culture dishes or detection cells, and measuring the cell traction force $\Delta S_t$ of the cells at adhesion time t by the following formula:

$$\Delta S_t = (K_{AT} - K_{BT})^{-1} [t_q^{AT} \Delta f_t^{AT} / fr^{AT} - tq^{BT} \Delta f_t^{BT} / fr^{BT}] \quad (1),$$

wherein in formula (1), $K_{AT}=2.75\times10^{-12}$ cm$^2$ dyn$^{-1}$ and $K_{BT}=-2.65\times10^{-12}$ cm$^2$ dyn$^{-1}$ are stress coefficients of the AT-cut quartz crystal and the BT-cut quartz crystal respectively; $fr^{AT}$ is the resonant frequency of the AT-cut quartz crystal, $fr^{BT}$ is the resonant frequency of the BT-cut quartz crystal, $tq^{AT}$ is the thickness of the AT-cut quartz crystal, $tq^{BT}$ is the thickness of the BT-cut quartz crystal, and the relationship between the thickness and frequency of each of the two cut types is determined by its frequency constant N, the frequency constants of the AT-cut and BT-cut quartz crystals are $N^{AT}=1.661$ MHz·mm=0.1661 MHz·cm and $N^{BT}=2.536$ MHz·mm=0.2536 MHz·cm, respectively; so for a quartz crystal of certain frequency, its thickness tq is also correspondingly determined, specifically: $tq^{AT}=0.1661/fr^{AT}$; $tq^{BT}=0.2536/fr^{BT}$. $\Delta f_t^{AT}$ and $\Delta f_t^{BT}$ are respectively the frequency shifts of the AT-cut and BT-cut quartz crystals at any time t relative to their reference points (e.g., stable values in the media or stable values after adhesions);

when $\Delta S_t$ is negative, it indicates that the stress on the cells is compressive, the cells are contracted, and the corresponding extracellular matrices are subjected to a tensile stress equal and opposite to the compressive stress; when $\Delta S_t$ is positive, the stress on the cells is a tensile stress, the cells are in spread status, and the corresponding extracellular matrices are subjected to a compressive stress equal and opposite to the tensile stress, that is, the conventional cell contraction or traction force, and it is known that animal cell microtubules mainly exert a compressive stress on cells, while actin filaments containing stress fibers exert a tensile stress on cells.

The cell adhesion molecules mainly include the following categories: 1) extracellular matrix molecules capable of interacting with transmembrane proteins and integrins, e.g., fibronectin, laminin, vitronectin, collagen, etc.; 2) extracellular matrix biomimetic molecules, e.g., RGD adhesion sequence polypeptides; 3) molecules capable of interacting with other receptors (e.g., cadherin) on the surface of cells; and 4) molecules interacting with the surface of the cell by other mechanisms to promote cell adhesion, e.g., poly-l-lysine, etc. Fetal bovine serum having certain ingredients generally is added to the cell culture medium, and the fetal bovine serum itself contains trace proteins that promote cell attachment, spreading and growth, so even if the sensor surface is not modified with cell adhesion molecules (e.g., bare gold electrodes), the adhesion to cells can also be achieved by adsorbing these ingredients in the medium. In addition, the cells themselves have the function of secreting extracellular matrices to promote their adhesion to the sensor surface.

Although the cell traction force generally refers to a force applied to the matrix by the formation of focal adhesions between the cells and the matrices, as long as the cells can adhere to the matrices, whether or not focal adhesions are formed, or even whether the adhesion is chemical or mechanical driven, a surface stress can be applied to the adhered substrate. In the absence of focal adhesion formation, the interaction of cells with substrate is referred to as a cell adhesion force. In addition, the processes such as cell growth, movement and differentiation also produce varying degrees of forces on substrate. In general, the order in which cells can produce forces on substrate is: force generated during division>traction force>adhesion force. All of these forces can be measured and studied in a real time, quantitative and continuous way using the technology of the present disclosure. Moreover, the present disclosure can be used for studying and comparing the dynamic effects of different cell adhesion molecules and various mechanical topographies on these force responses. In addition, the present disclosure can be used for studying the dynamic characteristics of cell generated forces under the stimulations of different internal and external environments, e.g., the effects of drugs.

The present disclosure is applicable to all adherent cells, including primary cells and passage cells. The present disclosure can be extended to suspension cells, including direct study on weak interaction between suspension cells and substrate, facilitated by modification of the substrate with molecules or materials that interact with the surfaces of suspension cells. The present disclosure is further extended to all cells, including prokaryotic cells and eukaryotic cells. That is, in addition to animal cells, the present disclosure can also be applied to all bacteria, fungi and plant cells.

The following further describes the present disclosure:

The core technology of the present disclosure is based on a piezoelectric double resonator technology. Specifically, AT-cut and BT-cut orientated crystals are used, having almost the same stress coefficient but opposite signs. The stress change can be estimated by the so-called double resonator technology according to the frequency shifts of two resonators in the same interface process. That is, as long as the conditions that the masses and stresses generated by an external deposit in the AT-cut and BT-cut surface deposition processes are identical are satisfied, the mass and stress accompanying the surface deposition process can be quantitatively estimated according to the thicknesses (or frequencies) and the frequency changes of the AT-cut and BT-cut crystals. This technology has been used for the measurement of dynamic surface stress changes accompanying by ion-sputtering metal film on a quartz crystal, hydrogen adsorption on metallic palladium and the phase transition of a carboxylic acid self-assembled thiol film induced by pH change, but has not been used for live cell studies. Before this, Tan et al. first proposed that the surface stress caused by cell adhesion is a major mechanism of cell adhesion induced quartz crystal microbalance (QCM) response. They assumed that the influence of mass was negligible, and treated cells as a Newtonian fluid. The dynamic stress change of the cell adhesion process was calculated after the force-frequency constant of the AT-cut quartz crystal was obtained by a scanning electrochemical microscopy (SECM). This work is very important, and shows the potential to measure the cell contraction or traction force using QCM technology, but with some limitations. Newtonian droplets have been used as a mechanical model of live cells, mainly for suspension cells, which is too simple to be applicable to adherent cells. The hypothesis may only be valid when there is only a weak interaction between the cells and the sensor, and the influence of the mass effect may also be the same. In fact, the number of cells used by the above researchers is 60,000 which could result in strong cell-cell interactions, and possibly forming a cell monolayer. Thus, the cells-sensor interaction is weak. In addition, the single AT-cut type crystal cannot determine the direction of cells generated surface stress. BT-cut quartz crystal has not been applied to live cell research. The present disclosure first proposes and utilizes AT-cut and BT-cut crystals of different orientations to realize real-time and quantitative measurement of the magnitude and direction (compressive or tensile stress) of surface stress (contraction or traction force) applied to the quartz crystals by cells during adhesion and the subsequent drug effect. In the absence of other factors, the stress change will cause equal but opposite frequency shift changes for the two oriented crystals. In particular, for AT-cut and BT-cut crystals having the same frequency and surface roughness and the same surface molecules modified in the same way should have the same response sensitivity to mass and viscoelasticity.

Therefore, the surface stress or cell traction force applied to the crystals at any time throughout the cell adhesion process can always be accurately estimated by the following formula:

$$\Delta S_t = (K_{AT} - K_{BT})^{-1} [t_q^{AT} \Delta f_t^{AT} / fr^{AT} - t_q^{BT} \Delta f_t^{BT} / fr^{BT}] \quad (1),$$

in which, $K_{AT} = 2.75 \times 10^{-12}$ cm² dyn⁻¹ and $K_{BT} = -2.65 \times 10^{-12}$ cm² dyn⁻¹ are stress coefficients of the AT-cut quartz crystal and the BT-cut quartz crystal respectively; $fr^{AT}$ is the resonant frequency of the AT-cut quartz crystal, $fr^{BT}$ is the resonant frequency of the BT-cut quartz crystal, $tq^{AT}$ is the thickness of the AT-cut quartz crystal, $tq^{BT}$ is the thickness of the BT-cut quartz crystal, all of which are constants. Therefore, the surface stress or traction force applied to the crystal by cells in the adhesion process or under the action of a drug can be quantitatively estimated according to the frequency shift $\Delta f_t^{AT}$, $\Delta f_t^{BT}$ (in Hz) of the AT-cut, and BT-cut crystals at any time t relative to their reference points (e.g., stable values in the cell culture media or stabile values before dosing) based on formula (1). The frequency of the quartz crystal is a digital signal, which can be easily, quickly and continuously acquired or measured by a frequency counting device or a specialized QCM instrument.

As for 9 MHz AT-cut and BT-cut crystals, $fr^{AT}=fr^{BT}=9$ MHz$=9\times10^6$ Hz, $tq^{AT}=0.0185$ cm, $tq^{BT}=0.0283$ cm.

Then, formula (1) is simplified to $$\Delta S_t = 2.058\times10^4(0.0185\Delta f_t^{AT} - 0.0282\Delta f_t^{BT}) \quad (2).$$

The unit of the surface stress $\Delta S_t$ obtained is dyn/cm. When $\Delta S_t$ is negative, it indicates that the stress on the cells is a compressive stress, the cells are contracted, and the corresponding extracellular matrix is subjected to a tensile stress equal and opposite to the compressive stress; when $\Delta S_t$ is positive, the stress on the cells is a tensile stress, the cells are in a spread status, and the corresponding extracellular matrix is subjected to a compressive stress equal and opposite to the tensile stress, that is, generally referred as cell contraction or traction force.

The core content of the present disclosure is to first propose and utilize the AT-cut and BT-cut double resonator quartz microbalance technology for quantitative measurement of the cell traction force. The double resonator technology used for surface stress measurement was first proposed by Errol P. EerNisse. The formulas used in the present disclosure are also based on EerNisse's achievements, but our research objects are cells. Except for the mass and surface stress considered by EerNisse, the cells also have certain viscoelasticity. We believe that the AT-cut and BT-cut quartz crystals of the same frequency have the same response to solution viscosity and density as proved by experiments with different weight percentages of sucrose aqueous solution, so it can be considered that the two cut types of the same frequency have consistent response to the viscoelasticity (of cells), and the cell traction force can still be quantitatively calculated using the formula in the present invention.

$K_{AT}$ and $K_{BT}$ in the formula are stress coefficients of AT-cut and BT-cut quartz crystals of given crystal orientations, respectively; and are constants. The relationship between the thickness and frequency of each of the two cut types is determined by its respective frequency constant N, and the frequency constants of the AT-cut and BT-cut quartz crystals are $N^{AT}=1.661$ MHz·mm$=0.1661$ MHz·cm and $N^{BT}=2.536$ MHz·mm$=0.2536$ MHz·cm, respectively. For a quartz crystal with definite resonant frequency fr, its thickness tq is also correspondingly determined, specifically: $tq^{AT}=0.1661/fr^{AT}$; $tq^{BT}=0.2536/fr^{BT}$. Therefore, if the frequency of the quartz crystal is higher, the crystal is thinner. Too thin crystal is fragile and difficult to process and operate, so the upper limits of the fundamental frequencies of the AT-cut and BT-cut quartz crystals are about 40 MHz and 60 MHz respectively. However, the operating frequency of the quartz crystal can be greatly improved by the following two methods: 1) etching the quartz crystal to a desired frequency thickness in the center of the quartz substrate by ion sputtering or the like, and then depositing a metal layer only to the etched portion to limit the oscillation of the quartz crystal to a small energy trap region; 2) operating the quartz crystal in overtone mode under different overtone frequencies of 3, 5, 7, 9, 11 etc., in addition to the fundamental frequency. Through these two methods, the current technologies can increase the operating frequency of quartz crystals to about 400 MHz. The lower limits of the operating frequencies of the AT-cut and BT-cut quartz crystals are about 0.5 MHz. Therefore, the operating frequency range of the AT-cut and BT-cut quartz crystals currently available for cell traction force measurement can reach 0.5-400 MHz, and the thicknesses of the corresponding AT-cut and BT-cut quartz crystals are respectively 5.5 μm-3.3 mm and 6.3 μm-5.1 mm.

The frequency changes of the AT-cut and BT-cut crystals caused by $\Delta S$ are given below respectively:

$$\Delta f_{r,s}^{AT} = f_{r,s}^{AT} - f_r^{AT} = f_r^{AT}K_{AT}\Delta S/tq^{AT} = K_{AT}f_r^{2,AT}\Delta S/N^{AT} \quad (3), \text{ and}$$

$$\Delta f_{r,s}^{BT} = f_{r,s}^{BT} - f_r^{BT} = f_r^{BT}K_{BT}\Delta S/tq^{BT} = K_{BT}f_r^{2,BT}\Delta S/N^{BT} \quad (4).$$

In the above two formulas, $f_{r,s}$ is the resonant frequency of the crystal under stress, and K, N and $f_r$ are stress coefficient, frequency constant and stress-free resonant frequency of the AT-cut or BT-cut quartz crystal, respectively. Thus, the frequency change caused by stress is proportional to the square of the operating resonant frequency of the crystal. From the above two formulas, the frequency change caused by the same magnitude of cell traction force at 300 MHz is 1,111 times that at 9 MHz. The 9 MHz quartz crystal can be used for detecting cell traction force generated by as less as 1,000-5,000 cells, so the 300 MHz quartz crystal is expected to detect individual cells and changes in their traction force. In addition, this extremely high-frequency double resonator sensing technology is also expected to be used for dynamic monitoring of forces accompanying molecular interactions (e.g., polymerization or depolymerization of polymers). The lower limit of the operating frequency of the quartz crystal is 0.5 MHz, so the technology of the present disclosure can be extended to tissues (e.g., blood vessels), organs (e.g., hearts, embryos) and even small animals and plants. Thus, the technology of the present disclosure is expected to be used for dynamic monitoring of forces generated from molecules to single cells, cell populations, tissues and organs, and even to different levels of small organisms.

Compared with the prior arts, the present disclosure has the following beneficial effects:

1) The method can measure the cell traction force in a real time, continuous and dynamic way in the cell adhesion process and under the action of a drug and the like, based on the dynamic monitoring of the frequencies of high-frequency AT-cut and BT-cut quartz crystals, without the need of using an optical microscopy. Digital frequency signals are measured, so the sampling speed is high (up to a set of data per 0.1 second). Since the technology is non-destructive and can be compatible with the structure of a culture dish and placed in a $CO_2$ incubator for long-term monitoring, the cell traction force accompanying cell functions such as cell movement, growth and differentiation can be monitored continuously for a long term. The fast response time, high sampling speed and continuous, dynamic and long-term monitoring capability of the proposed method are not achievable by the conventional cell traction force methods.

2) The method can be used for quantitative measurement of the magnitude and direction of the total traction force under different cell numbers (e.g., 100-60000) or different cell surface densities. By increasing the frequency of the crystal and/or patterning cells, the number of the examined cells can be further reduced, and even single cells can be measured. That is, the present disclosure is expected to achieve quantitative measurement of the cell traction force from a single cell to a cell monolayer.

3) Animal adherent cells not only interact with adjacent cells, but also contact and interact with extracellular matrix. Another characteristic of the technology of the present disclosure lies in that it can quantitatively examine the effects of adhesion molecules on cell traction force and correlate with cell functions and behaviors by modifying different extracellular matrix components and cell adhesion molecules on the surface of a sensor and changing their surface densities. In addition, the use of optically transparent sensor electrodes and fluorescent labeled focal adhesion proteins can correlate the cell traction force measured by the sensor with the morphology (degree of spreading) of cells and the structure of focal adhesions. The cell traction force is mainly applied to the extracellular matrix through the focal adhesions; the abundant signal protein molecules on the focal adhesions can also transmit the physical and chemical information in the perceived extracellular microenvironment to the interior of cells to trigger a series of intracellular biochemical reactions, thereby producing important effects on cell functions and behaviors (e.g., change in cytoskeletal structure, change in gene expression, apoptosis, etc.). Therefore, the present disclosure provides a novel and effective tool for quantitative research on cell mechno-sensing and applications in the fields of cell biology etc.

4) The present disclosure can be further extended to the high throughput measurements of cells generated traction forces, for example, the outer circumferences of AT-cut and BT-cut quartz crystals of different frequencies can be bonded to a piece of inert glass or a plastic perforated substrate by a soft adhesive, to prepare piezoelectric anti-acoustic coupled resonant chips of different throughput numbers. The high-throughput piezoelectric anti-acoustic coupled resonant chips are particularly suitable for screening and evaluating drugs that affect cell actomyosin contraction and the like.

In summary, the present disclosure differs from the measurement principle based on substrate deformation. The present disclosure adopts the sensor technology of direct sensing of cells generated force, where the magnitude and direction of the cell traction force is directly measured by means of the change of the sensor output signal caused by the surface stress applied to the sensor, so optical microscopy for graphing and fluorescent labeled microbeads are not required. The present disclosure can be applied to the quantitative measurement of the magnitude and direction of the total traction force of a cell population under different cell numbers or different cell-cell interactions. The sensing technology of the present disclosure is non-destructive, and can be used for real-time, continuous and dynamic measurement of cell traction force in the process of cell adhesion under different extracellular matrices and subsequent processes of cell movement, growth, differentiation and the like under the external stimulations of drugs and the like. The sensor used in the present disclosure can be placed at the bottom of a conventional cell culture dish to be compatible with the configuration of a common culture dish (including porous plates of different throughput numbers), so that the present disclosure can be extended to broad fields of cell biology, drug screening and the like.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

DETAILED DESCRIPTION OF THE PRESENT DISCLOSURE

Figure 1:
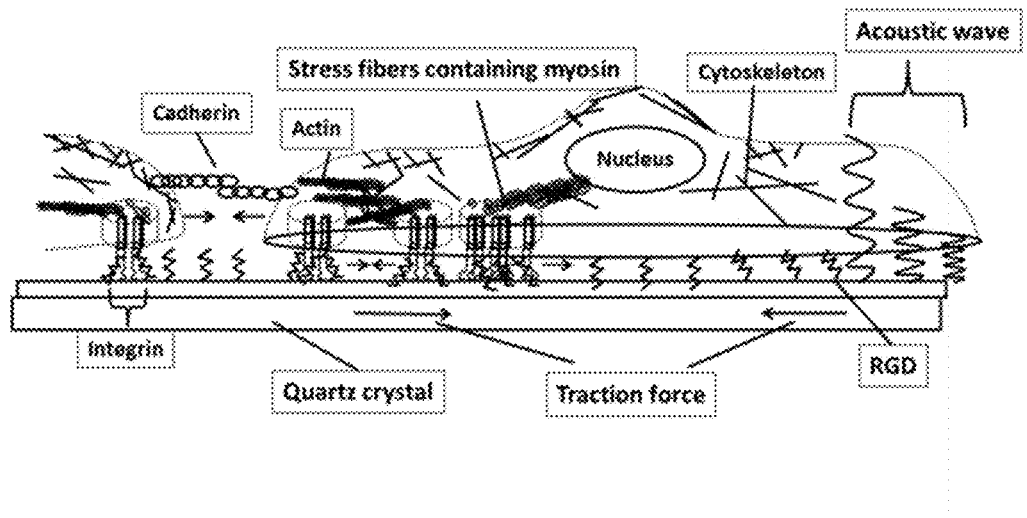
FIG. 1 is a schematic diagram of cell structure-mechanics and QCM acoustic detection.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure is thorough and complete, and will fully convey the scope of the invention to those skilled in the art. Like reference numerals refer to like elements throughout.

Figure 2:
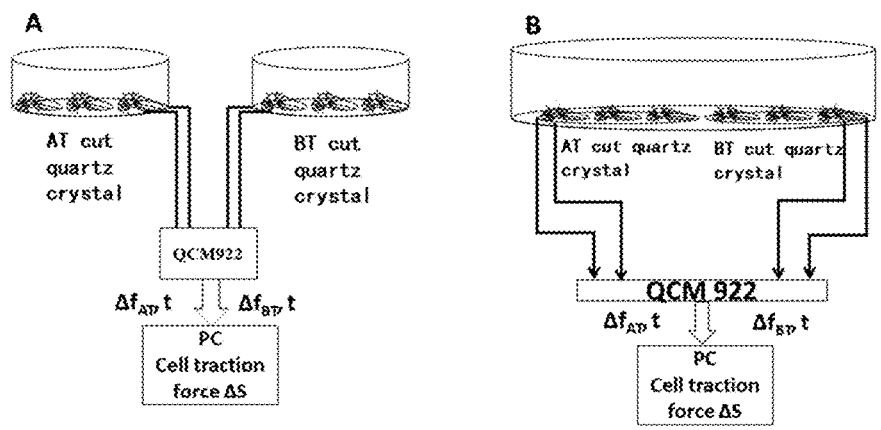
FIG. 2 shows two configurations for cell traction force detection.

FIG. 2 shows two configurations for quantitatively measuring the cell traction force using the AT-cut and BT-cut double resonator technology. In FIG. 2A, the AT-cut and BT-cut crystals are in two different culture dishes or detection cells. At this time, the AT-cut and BT-cut crystals have the same frequency and surface morphology and/or the same surface adhesion molecules modified. After the same number and quality of cells of the same batch are added to the two detection cells, the cell traction force can be quantitatively measured from formula (1) by monitoring the frequency changes of the two crystals in real time. In FIG. 2B, the AT-cut and BT-cut crystals are in the same culture dish or detection cell, and the two crystals are also required to have the same frequency and surface morphology and/or the same surface adhesion molecules modified, and after a certain number of cells are added to the detection cell, the cell traction force can be quantitatively measured from formula (1) by detecting the frequency changes of the two crystals in real time. The measurement of the cell traction force requires no microscopy, so the metal electrode and the modified molecules and materials on the surface of the quartz crystal are not required to be transparent, and can be any material, which is another advantage of the method. Specifically, the surface of the quartz crystal may be covered by metal gold or non-metal $SiO_2$ or the like which is biocompatible with cells.

Figure 3:
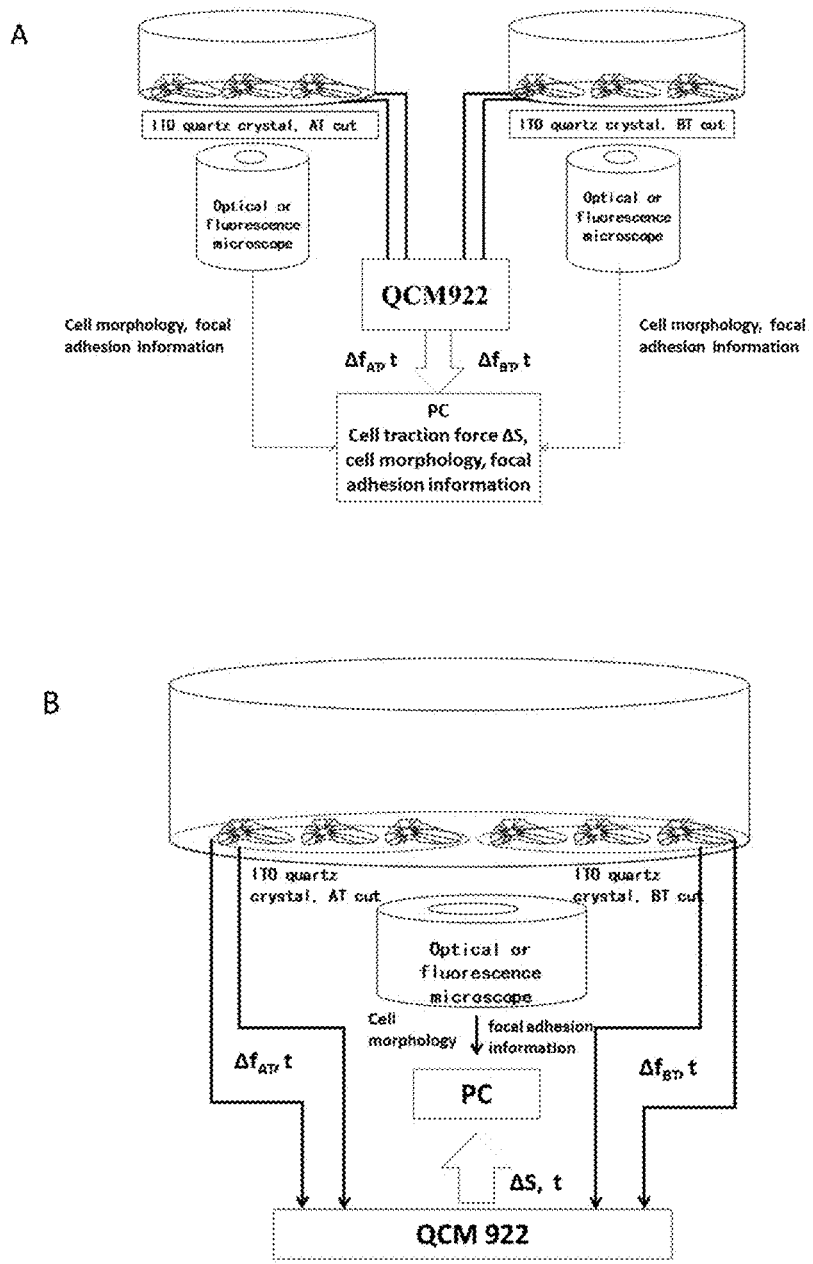
FIG. 3 shows two configurations for simultaneously measuring cell traction force, cell morphology, and focal adhesion information.

Ideally, in order to acquire dynamic information such as cell morphology and focal adhesions accompanying the change in the cell traction force, the QCM crystal can be used in conjunction with an optical or fluorescence microscopy. In this case, an optically transparent QCM electrode, such as an ITO electrode, is required. Similarly, two different configurations can be used, as shown in FIGS. 3A and 3B.

The real-time and quantitative measurement method for cell traction force includes the following steps:

(1) placing an AT-cut quartz crystal and a BT-cut quartz crystal in two separate culture dishes or detection cells, the AT-cut quartz crystal having the same frequency, surface morphology and/or modified surface adhesion molecules as the BT-cut quartz crystal; and (2) adding cells to be tested to the culture dishes or the detection cells, and measuring the cell traction force $\Delta S$ by the following formula:

$$\Delta S_t = (K_{AT} - K_{BT})^{-1} [t_q^{AT} \Delta f_t^{AT} / fr^{AT} - t_q^{BT} \Delta f_t^{BT} / fr^{BT}],$$

in which, $\Delta S_t$ is the traction force of cells at the adhesion time t; $K_{AT} = 2.75 \times 10^{-12}$ cm$^2$ dyn$^{-1}$ and $K_{BT} = -2.65 \times 10^{-12}$ cm$^2$ dyn$^{-1}$ are stress coefficients of the AT-cut quartz crystal and the BT-cut quartz crystal of given crystal orientations, respectively; $fr^{AT}$ and $fr^{BT}$ are the resonant frequencies of the AT-cut and BT-cut quartz crystals, respectively; $tq^{AT}$ and $tq^{BT}$ are the thicknesses of the AT-cut and BT-cut quartz crystals, respectively. All the above are constants. $\Delta f_t^{AT}$ and $\Delta f_t^{BT}$ are respectively the frequency shifts of the AT-cut and BT-cut quartz crystals at any time t relative to their reference points (e.g., a stable value in a medium).

Cell Traction Force Double Resonator Technology Experiment

The steps for measuring the cell traction force by using bare gold electrode AT-cut and BT-cut quartz crystals are as follows:

1) dripping 1 drop of Piranha solution (80° C. 1:3 (v:v) 30% $H_2O_2$:$H_2SO_4$) to the center of each quartz crystal gold electrode for about 30 s, then rinsing with distilled water, drying with nitrogen, and repeating this step by 3 times;

2) assembling the crystals in a Teflon well cell;

3) cleaning the Teflon cell twice with distilled water, then adding about 300 µL of sterilized water, and putting into a 5% $CO_2$ incubator at 37° C.;

4) checking to make sure that the 8-channel QCM instrument QCA922 has crystal resonant frequency and dynamic resistance outputs, connecting detection cells in turn, determining that each detection cell (e.g., two AT-cut crystal detection cells, two BT-cut crystal detection cells) works, and starting the software to acquire data;

5) removing the sterilized water after the data corresponding to each channel is stable, cleaning twice with sterilized water, then cleaning with PBS, add 52 µL of DMEM medium containing fetal bovine serum, and acquiring QCM resonant frequency (f) and dynamic resistance (R) data for 2 h; adding 250 µL of medium containing a certain number (e.g., 20,000) of H9C2 rat cardiomyocytes or human umbilical vein endothelial cells (HUVECs), continuously acquiring f and R data for about 20 h. The QCM relative frequency shift Δf and dynamic resistance change ΔR of each channel caused by the adhesion of cells at different adhesion time are determined by subtracting the corresponding QCM stable values in media of the channel at the time (t).

6) After the experiment, collecting the medium, gently washing with PBS, adding trypsin for digestion, and counting the cells in the collected fraction with a cytometer;

7) Quantitatively measuring the dynamic change ΔS in the cell traction force during the cell adhesion process according to the frequency shifts $\Delta f_t^{AT}$ and $\Delta f_t^{BT}$ of the paired AT-cut and BT-cut quartz crystals at the time t:

$$\Delta S_t = (K_{AT} - K_{BT})^{-1} [t_q^{AT} \Delta f_t^{AT}/fr^{AT} - tq^{BT} \Delta f_t^{BT}/fr^{BT}] \quad (1),$$

in which, $\Delta S_t$ is the traction force of cells at the adhesion time t; $K_{AT} = 2.75 \times 10^{-12}$ cm² dyn⁻¹ and $K_{BT} = -2.65 \times 10^{-12}$ cm²dyn⁻¹ are stress coefficients of the AT-cut and BT-cut quartz crystals of given crystal orientations, respectively, and are constants. $fr^{AT}$ and $fr^{BT}$ are the resonant frequencies of the AT-cut and BT-cut quartz crystals, respectively; $tq^{AT}$ and $tq^{BT}$ are the thicknesses of the AT-cut and BT-cut quartz crystals, respectively, and are constants. Therefore, the surface stress or traction force applied to the crystal by cells in the adhesion process or under the action of a drug can be quantitatively measured according to the frequency shifts $\Delta f_t^{AT}$, $\Delta f_t^{BT}$ (in Hz) of the AT-cut crystal, the BT-cut crystal at any time t relative to its reference point (e.g., a stabile value in the medium or a stabile value before dosing) based on formula (1). The frequency of the quartz crystal is a digital signal, which can be easily, quickly and continuously acquired or measured by a frequency counting device or a QCM special instrument. The crystal frequency used in the experiment of the present disclosure is 9 MHz, where $tq^{AT} = 0.0185$ cm, and $tq^{BT} = 0.0282$ cm. Thus, formula (1) can be simplified as:

$$\Delta S_t = 2.058 \times 10^4 (0.0185 \Delta f_t^{AT} - 0.0282 \Delta f_t^{BT}) \quad (2)$$

The Steps for Measuring the Cell Traction Force with AT-Cut and BT-Cut Quartz Crystals Modified with Specific Cell Adhesion Molecules RGD and Fibronectin are as Follows:

1) cleaning with anhydrous ethanol and Millipore water, and blowing AT-cut and BT-cut 9 MHz crystals with nitrogen;
2) dripping 1 drop of Piranha solution (80° C. 1:3 (v:v) 30% $H_2O_2$:$H_2SO_4$) to the quartz crystal gold electrode for treating 30 s, rinsing with Millipore water and anhydrous ethanol, blowing with nitrogen, and repeating 3 times. Dripping the anhydrous ethanol onto the electrode to stand for a few minutes, rinsing with sterile water, and blowing with nitrogen;
3) installing the surface treated AT-cut and BT-cut quartz crystals into Teflon well cells;
4) adding a mixed anhydrous ethanol solution of 20 mM 3-mercaptopropionic acid and 1 mM triethylene glycol mono-11-mercaptoundecyl ether to the Teflon cell at room temperature, and standing overnight in the dark;
5) taking out the solution, and rinsing with sterile water; adding a PBS buffer solution (pH=5.5) with 150 mM EDC and 30 mM NHS dissolved therein, and standing for about 30 min;
6) taking out the solution, and rinsing with PBS buffer solution (pH=5.5) and sterile water; adding a PBS solution of KRGD or fibronectin of different concentrations, and standing for 1-2 h (RGDK) or overnight (fibronectin);
7) taking out the solution, and rinsing with sterilized PBS and sterile water to obtain KRGD or fibronectin modified gold electrodes. Adding 20,000 HUVEC or H9C2 cells, and starting QCM for monitoring;

8) collecting the medium after the experiment, gently wash with PBS, adding trypsin for digestion, and measuring the cells in the collected fraction with a cytometer; and 9) Quantitatively estimating the dynamic change ΔS in the cell traction force during the cell adhesion process according to the frequency shifts $\Delta f_t^{AT}$ and $\Delta f_t^{BT}$ of the AT-cut and BT-cut quartz crystals modified with the same concentration of RGD or fibronectin at the time t based on formula (2).

Experimental Steps for Effects of Cardiovascular Stimulating Drug Isoprenaline (ISO) and Inhibitory Drug Verapamil (VRP) on Traction Force of H9C2 Rat Cardiomyocytes Take four Teflon well cells, two identical 9 MHz AT-cut gold electrode crystals and two identical 9 MHz BT-cut gold electrode crystals. Based on the aforementioned steps of measuring the cell traction force with bare gold electrode AT-cut and BT-cut quartz crystals, add 20,000 H9C2 cells to the four Teflon cells respectively, culture cells for 20 h, then take 5 μL of the culture solution out from the four Teflon cells respectively, add 5 μL of 10 μM ISO (final concentration 125 nM) and 5 μL of 2 μM VRP (final concentration 25 nM) to the two AT-cut and BT-cut crystal detection cells respectively, continuously monitor for 20 h, and collect data.

Experimental Steps for Effects for Vascular Endothelial Barrier Function Destruction Drug Thrombin and Protective Drug Y-27632 on Traction Force of Human Umbilical Vein Endothelial Cells Take four Teflon well cells, two identical 9 MHz AT-cut gold electrode crystals and two identical 9 MHz BT-cut gold electrode crystals. Based on the aforementioned steps of measuring the cell traction force with bare gold electrode AT-cut and BT-cut quartz crystals, add 300 μL DMEM medium to the four Teflon cells respectively, and collect data for about 2 h; add 300 μL of mediums containing 20,000 human umbilical vein endothelial cells respectively, collect data for about 24 h, then add the drugs thrombin and Y-27632 to the final concentrations, and continue to collect data for about 24 h.

Experimental Steps for Verification of the Established Methods with Drugs Blebbistatin and Nocodazole are as Follows:

Based on the aforementioned steps of quantitatively measuring the cell traction force with RGD and fibronectin modified AT-cut and BT-cut quartz crystals, use the 9 MHz AT-cut and BT-cut quartz crystals modified by 50 μg/mL KRGD and 20 μg/mL fibronectin, then add 20,000 human umbilical vein endothelial cells, detect the adhesion process by QCM for about 17 h, add 1.22 μM blebbistatin or 0.5 μM nocodazole (final concentration) to the AT-cut and BT-cut crystal detection cells respectively, continue to monitor for about 10 or 5 hours, collect data, and obtain the change characteristics of the cell traction force in the cell adhesion process and under the actions of blebbistatin and nocodazole drugs.

Experimental Steps for Effects of Different Concentrations of EGTA on Traction Force of Human Umbilical Vein Endothelial Cells Based on the aforementioned steps of measuring the cell traction force with bare gold electrode AT-cut and BT-cut quartz crystals, clean the 9 MHz AT-cut and BT-cut gold electrode crystals, and install the crystals into Teflon well cells. Add 400 μL of serum-free DMEM medium to the four Teflon cells respectively, and collect data for about 2 h. Add 200 μL of mediums containing 50,000 umbilical vein endothelial cells respectively, collect data for about 24 h, then add EGTA dissolved into PBS to the final concentrations of 1 mM, 10 mM and 50 mM, and continue to collect data for about 2-15 h.

Figure 4:
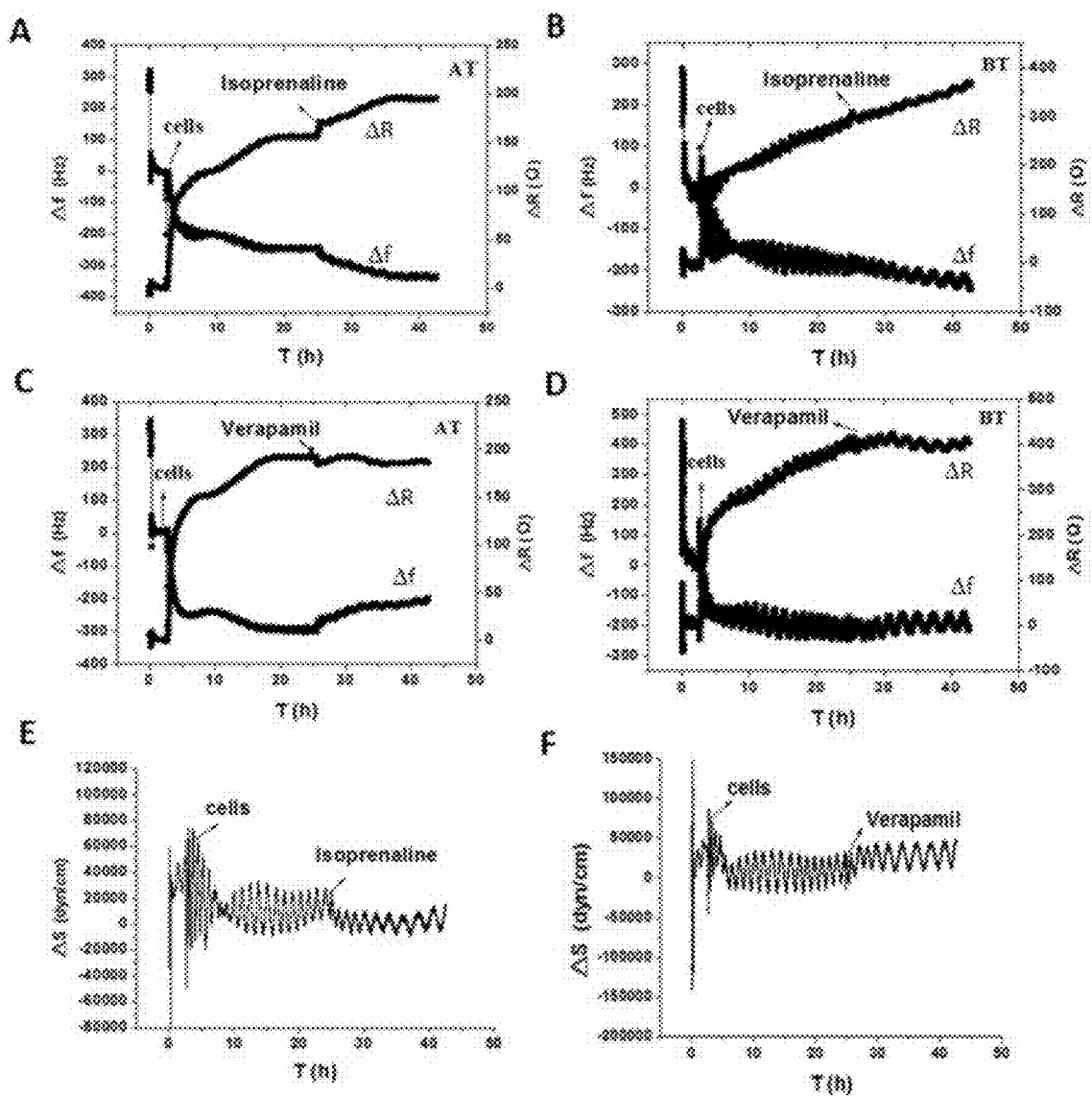
FIG. 4: example: dynamic QCM adhesion and force response curves under adhesion of 20,000 H9C2 rat cardiomyocytes (added at the first arrow) to AT-cut and BT-cut bare gold electrodes, and under the actions of 125 nM positive inotropic drug isoprenaline and 25 nM negative inotropic drug verapamil (the final concentration added at the second arrow). (A) Frequency shift and dynamic resistance change curve under adhesion and isoprenaline action, AT-cut; (B) Frequency shift and dynamic resistance change curve under adhesion and isoprenaline action, BT-cut; (C) Frequency shift and dynamic resistance change curve under adhesion and verapamil action, AT-cut; (D) Frequency shift and dynamic resistance change curve under adhesion and verapamil action, BT-cut; (E) Dynamic cell traction force change curve under adhesion and isoprenaline action; (F) Dynamic cell traction force change curve under adhesion and verapamil action.

Dynamic Changes of Cell Traction Force During Adhesions of Rat Cardiomyocytes and Under the Treatments of Cardiovascular Inotropic Drugs Given below are dynamic QCM responses during the adhesion of rat myocardial H9C2 cells followed by the treatments of positive inotropic drug ISO and negative inotropic drug VRP detected with bare gold 9 MHz AT-cut and BT-cut quartz crystals. The results are shown in FIG. 4. The bare gold electrode achieved non-specific adhesion to H9C2 cells by adsorbing the adherent factor contained in 10% fetal bovine serum in DMEM. As shown in FIG. 4A and FIG. 4B, with the addition of ISO, the f (frequency) of the two bare gold electrodes deposited AT-cut and BT-cut crystals decreased, and R (dynamic resistance) increased. The results under the action of negative inotropic drug VRP are shown in FIG. 4C and FIG. 4D, wherein as VRP is added, QCM f increased, and R decreased. The results are consistent with those of the previous cell adhesion tests and drug experiments obtained with AT cut crystals. In addition, the dynamic changes of the surface stress or traction force $\Delta S$ applied to the quartz crystal by cells in the cell adhesion process and under the action of the drug were quantitatively determined from double resonator AT-cut and BT-cut frequency shifts based on formula (2) (see FIG. 4E, FIG. 4F). The results of formula (2) show that when $\Delta S$ is negative, the force borne by the cells is compressive stress (during cell contraction or positive inotropic effect); and when $\Delta S$ is positive, the force borne by the cells is tensile stress (during cell spreading or negative inotropic effect). Due to the limited adhesion of cells to the bare gold electrode, the result of FIG. 4 shows that $\Delta S$ fluctuates around 0, indicating that the cells are not well spread on the bare gold electrode under the experimental condition, and the cells are still contracted to some extent. Under the action of the positive inotropic drug ISO, the cell contraction is strengthened, so the cell traction force decreases and changes negatively. Under the action of the negative inotropic drug VRP, the cells are relaxed and spread, and the cell traction force increases and changes positively.

Figure 5:
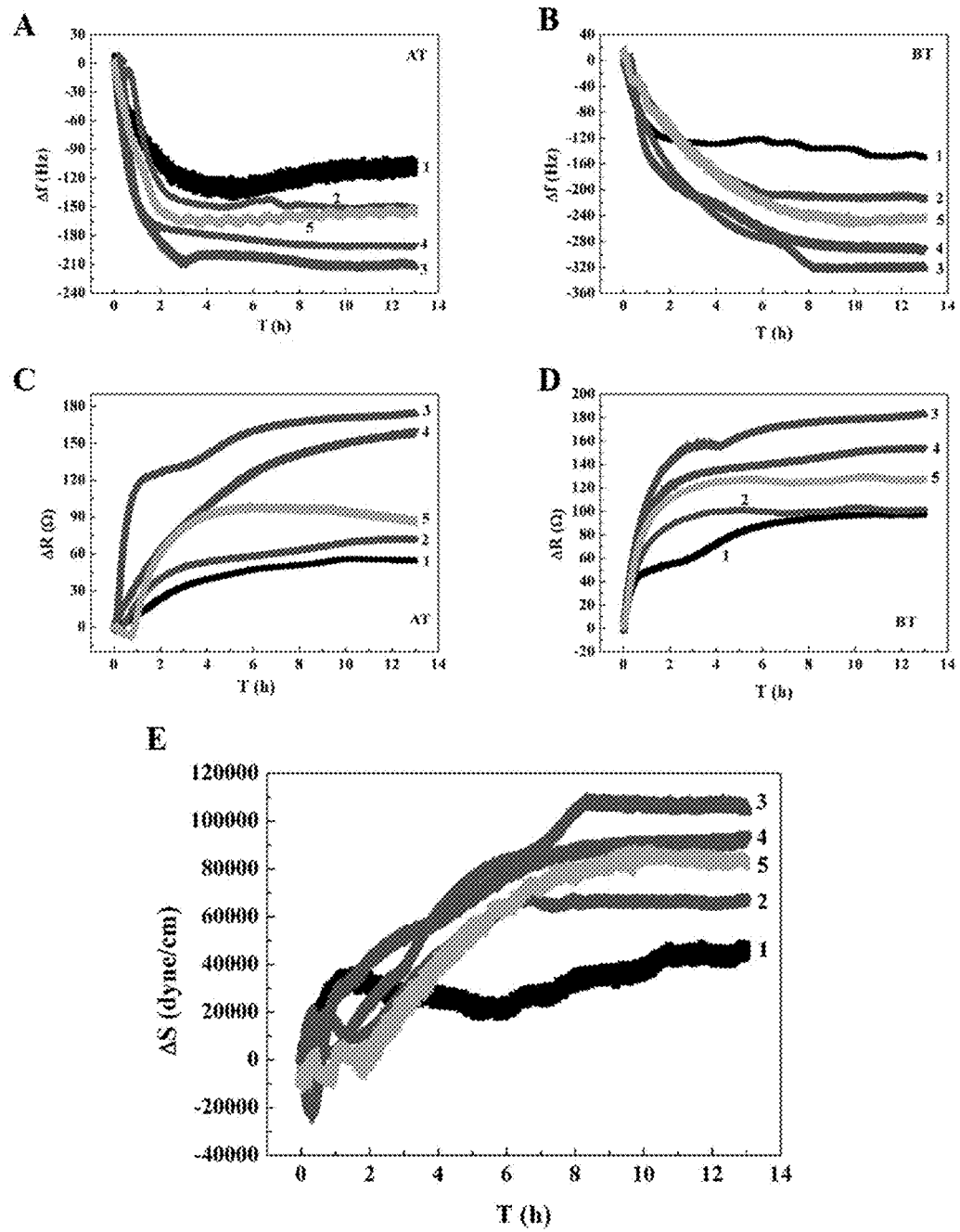
FIG. 5: example: QCM frequency shift, dynamic resistance change and traction force dynamic response curves during adhesion of 20,000 human umbilical vein endothelial cells to 9 MHz AT-cut and BT-cut quartz crystal gold electrodes modified at different KRGD concentrations. (A) Frequency shift response of RGD modified AT-cut crystal; (B) Frequency shift response of RGD modified BT-cut crystal; (C) Dynamic resistance change of RGD modified AT-cut crystal; (D) Dynamic resistance change of RGD modified BT-cut crystal; (E) Dynamic change in cell traction force of RGD modified crystal.

Changes in Cell Traction Force Accompanying Adhesion of Human Umbilical Vein Endothelial Cells to KRGD Modified Gold Electrodes After the 9 MHz AT-cut and BT-cut quartz crystal gold electrodes are modified with different surface density of cell-specific adhesion polypeptides RGD at different KRGD concentrations (0 μg/mL, 25 μg/mL, 50 μg/mL, 75 μg/mL, 100 μg/mL), the QCM frequency shift response and dynamic changes of cell traction force during the adhesion of 20,000 HUVECs in DMEM media containing 2% fetal bovine serum are shown in FIG. 5, numbers 1-5 correspond to the above mentioned 5 RGD concentrations, respectively. The frequency shift response curves of AT cut and BT cut show that the quartz crystal modified at the medium KRGD concentration (50 μg/mL) has best adhesion to cells, maximum frequency shift (FIG. 5A and FIG. 5B), and maximum dynamic resistance change (FIG. 5C and FIG. 5D). The results of FIG. 5E show that the cell traction force $\Delta S$ is positive, and as time increases, $\Delta S$ rapidly increases to an extreme value at about 8 hours, and then decreases. Therefore, the cells are well spread on the RGD modified surface, the force borne by the cells is tensile stress, and $\Delta S$ is positive. Consistent with the QCM frequency shift response results, the RGD modified surface created at 50 μg/mL KRGD gives maximum cell traction force, so it is believed that the cells interact well with RGD and are well spread at the optimized RGD surface density. With the bare gold electrodes (0 μg/mL RGD concentration), the response of the sensor is minimum. The QCM responses produced by the cells on the RGD modified surface created at higher RGD concentrations (75 μg/mL and 100 μg/mL) are medium, which may be caused by the fact that the interaction of cells with the QCM sensor at higher RGD concentrations is weaker than that created at the 50 μg/mL RGD of the optimal adhesion effect on cells because the orientation of RGD is affected by steric hindrance.

Figure 6:
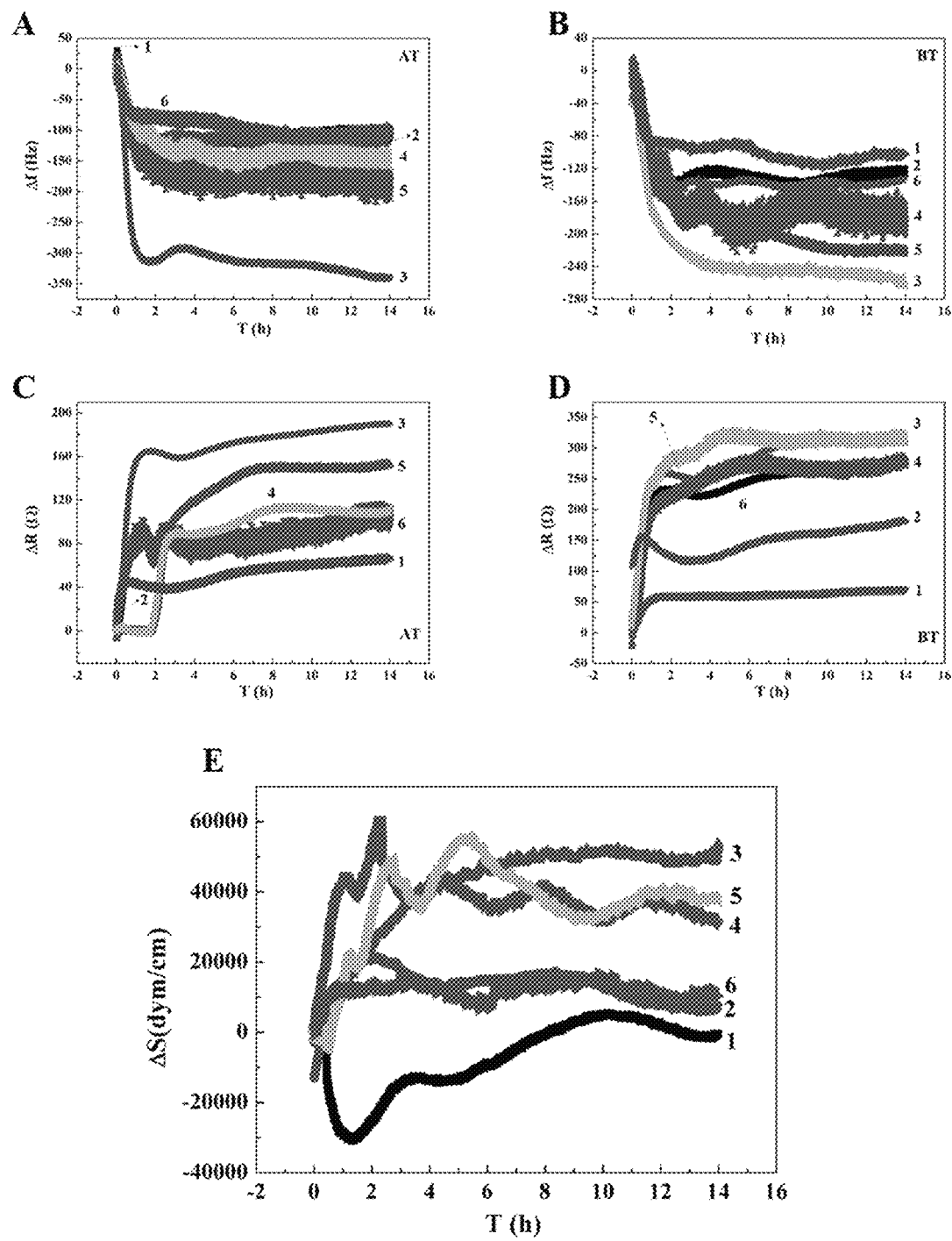
FIG. 6: example: QCM frequency shift, dynamic resistance change and traction force dynamic response curves of adhesion of 20,000 human umbilical vein endothelial cells to 9 MHz AT-cut and BT-cut quartz crystal gold electrodes modified at different fibronectin concentrations. (A) Frequency shift response of fibronectin modified AT-cut crystal; (B) Frequency shift response of fibronectin modified BT-cut crystal; (C) Dynamic resistance change of fibronectin modified AT-cut crystal; (D) Dynamic resistance change of fibronectin modified BT-cut crystal; (E) Dynamic change in cell traction force of fibronectin modified crystal.

Changes in Cell Traction Force Accompanying Adhesion of Human Umbilical Vein Endothelial Cells to Fibronectin Modified Gold Electrodes FIG. 6 shows the QCM frequency shift and dynamic resistance response of 20,000 HUVECs cell adhesion and dynamic changes in cell traction force in DMEM media containing 2% fetal bovine serum, after the 9 MHz AT-cut and BT-cut quartz crystal gold electrodes were modified at different fibronectin (FN) concentrations (0 μg/mL, 10 μg/mL, 20 μg/mL, 30 μg/mL, 40 μg/mL, 50 μg/mL). FIG. 6 also shows the results contrasts of the bare gold electrodes, numbers 1-6 correspond to the above mentioned 6 FN concentrations, respectively. It can be seen that the QCM frequency shift and the dynamic resistance change caused by adhering 20,000 HUVECs to the bare gold electrode are minimum, indicating that the adhesion to cells is the weakest at this time, the cells are not well spread and are mainly contracted, and the cell traction force $\Delta S$ is negative. However, as the adhesion time increases, the surface of the electrode may adsorb adherent factors beneficial to cell adhesion and extracellular matrix factors secreted by the cells, so that $\Delta S$ changes positively, and the cells are gradually spread and are finally close to the value of the cell traction force on the gold electrode modified at the low FN concentration (10 μg/mL). After the gold electrode is modified with FN, the cell traction force $\Delta S$ is positive, indicating that the cells are spread well and apply compressive stress to the crystal, that is, contractile traction force. By comparing the responses of the gold electrode $\Delta S$ modified at the six FN concentrations (FIG. 6E), the results show that, like the RGD situations, $\Delta S$ is maximum and stable at about medium concentration (20 μg/mL), and the QCM frequency shift and dynamic resistance response are also maximum. At the low FN concentration (10 μg/mL) and the highest FN concentration (50 μg/mL) tested, the cell traction forces are close and the least, and the corresponding QCM frequency shift and dynamic resistance change response are also the least. The QCM frequency shift and dynamic resistance change responses at the higher FN concentrations (30 μg/mL, 40 μg/mL) are medium, and the corresponding $\Delta S$ response increases fastest at the beginning, but fluctuates with time and attenuates to some extent, so the final stable value is lower than the $\Delta S$ value at the medium concentration (20 μg/mL).

Figure 7:
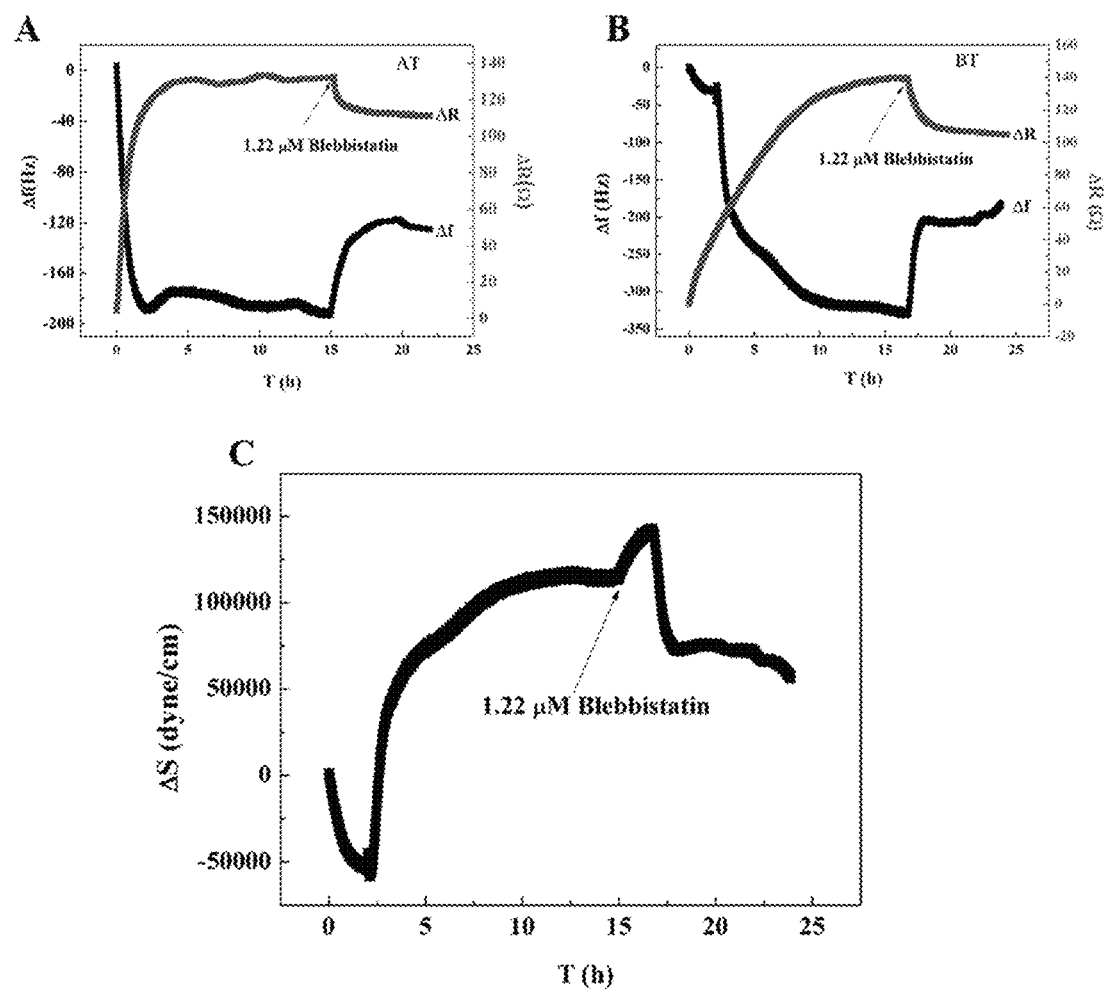
FIG. 7: example: QCM frequency shift, dynamic resistance change and cell traction force dynamic response curves in adhesion of 20,000 human umbilical vein endothelial cells to 9 MHz AT-cut and BT-cut quartz crystal gold electrodes modified at the concentration of 50 µg/mL KRGD, and under the action of 1.22 µM blebbistatin drug. (A) Frequency shift and dynamic resistance response of AT-cut crystal; (B) Frequency shift and dynamic resistance response of BT-cut crystal; (C) Dynamic change in cell traction force.
Figure 8:
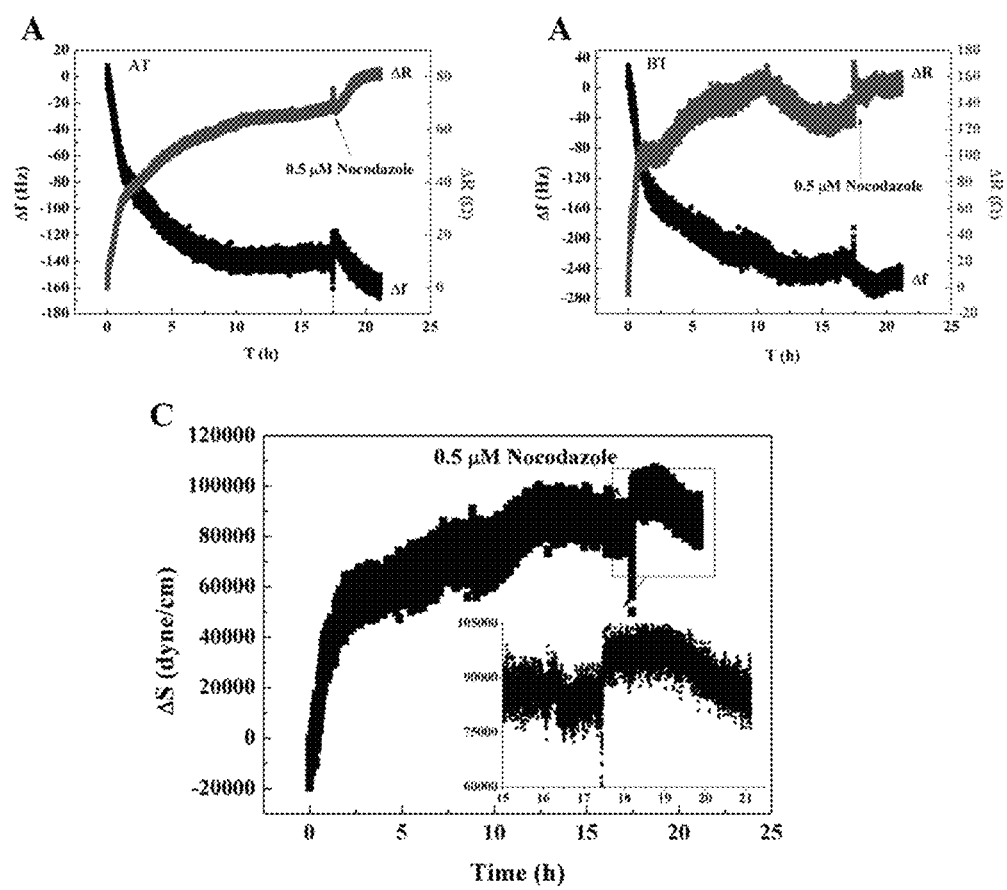
FIG. 8: example: QCM frequency shift, dynamic resistance change and cell traction force dynamic response curves in adhesion of 20,000 human umbilical vein endothelial cells to 9 MHz AT-cut and BT-cut quartz crystal gold electrodes modified at the concentration of 20 µg/mL fibronectin, and under the action of 0.5 µM nocodazole drug. (A) Frequency shift and dynamic resistance response of AT-cut crystal; (B) Frequency shift and dynamic resistance response of BT-cut crystal; (C) Dynamic change in cell traction force.

Dynamic Responses of Cell Traction Force Under the Actions of Drugs Blebbistatin and Nocodazole In order to verify the established piezoelectric cell force sensing method, we investigated the QCM response under the action of a myosin II inhibitor blebbistatin by using the quartz crystals modified at the 50 μg/ml RGD concentration. FIG. 7 shows that the cell traction force $\Delta S$ decreases under the action of blebbistatin. Blebbistatin is a non-myosin type II atpase (ATP) inhibitor. The result here is consistent with the conclusion reported in other methods of the literature that blebbistatin reduces the cell traction force. In addition, we also investigated the effect of a microtubule inhibitor nocodazole on the mechanical properties of cells, indicating that under the action of 0.5 µM nocodazole, the cell traction force increases at the beginning and then decreases (FIG. 8). Microtubules, as a rigid structure in the cytoskeleton, exert compressive stress to cells, and determine the cell force balance together with cytoskeletal actin filaments exerting tensile stress to cells. The microtubule inhibitor nocodazole depolymerizes the microtubules, so the cell traction force increases in the initial phase. As the acting time of nocodazole increases, the intracellular rigid microtubules are further lost, cell contraction and focal adhesions decrease, resulting in a decrease in the cell traction force. This is consistent with the results reported by the cell traction force microscopy in the literature.

Figure 9:
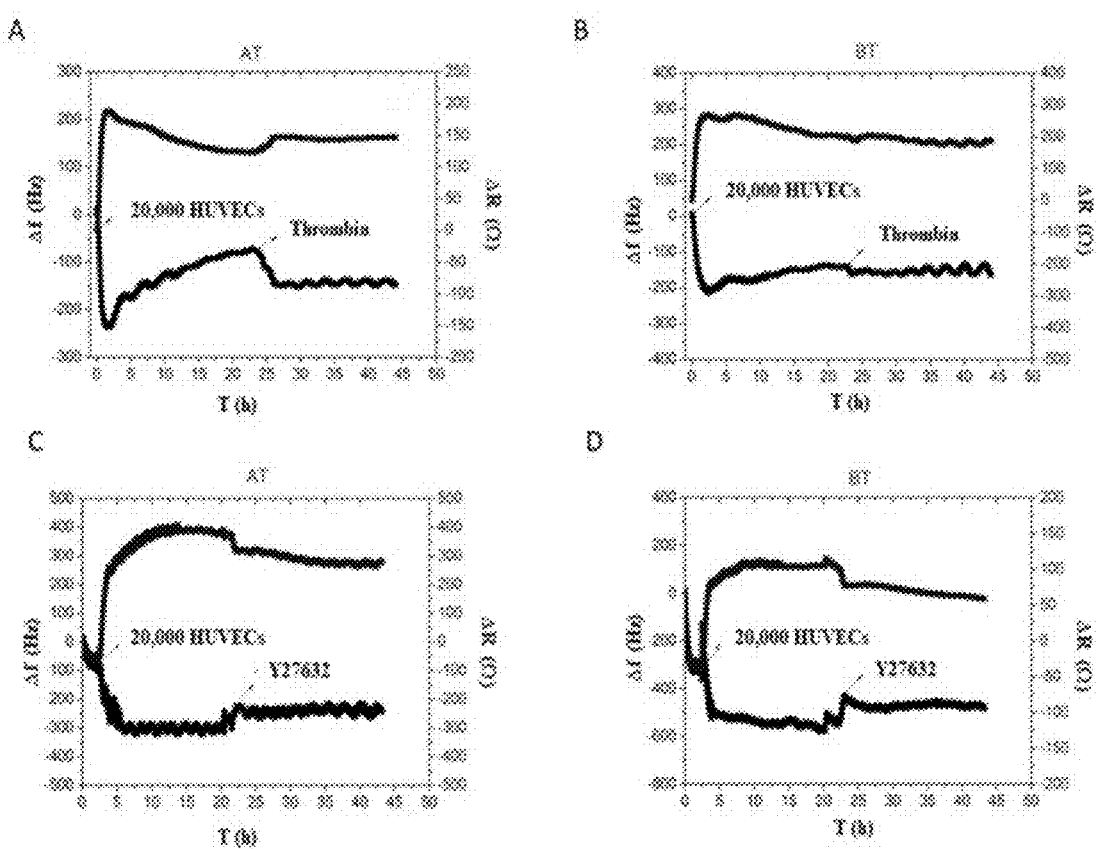
FIG. 9: example: dynamic QCM adhesion and force response curves under adhesion of 20,000 human umbilical vein endothelial cells (added at the first arrow) to AT-cut and BT-cut bare gold electrodes, and under the actions of 0.1 unit/mL vascular endothelial barrier function destruction drug thrombin and 0.5 µM endothelial barrier function protection drug Y-27632 (the final concentration added at the second arrow). (A) Frequency shift and dynamic resistance change curve under adhesion and thrombin action, AT-cut; (B) Frequency shift and dynamic resistance change curve under adhesion and thrombin action, BT-cut; (C) Frequency shift and dynamic resistance change curve under adhesion and Y-27632 action, AT-cut; (D) Frequency shift and dynamic resistance change curve under adhesion and Y-27632 action, BT-cut; (E) Dynamic cell traction force change curve under adhesion and thrombin action; (F) Dynamic cell traction force change curve under adhesion and Y-27632 action.

Effects of Vascular Endothelial Barrier Function Modulation Drugs Thrombin and Y-27632 on Cell Traction Force FIG. 9 shows curves of changes in frequency, dynamic resistance and cell traction force of 9 MHz AT-cut and BT-cut crystals caused by vascular endothelial barrier destruction drug thrombin and protective drug Y-27632 acting on human umbilical vein endothelial cells. It can be seen that under the action of thrombin, the frequency shift of the crystals decreases and the dynamic resistance increases slightly, indicating that the cell adhesion is enhanced and the cell traction force increases. Under the action of Y-27632, the frequency shift of the crystals decreases and the dynamic resistance decreases, indicating that the cell adhesion is weakened and the cell traction force decreases. The vascular endothelial barrier destruction reagent thrombin is a cytoskeletal contraction agonist that increases the cell traction force and the cell permeability. The role of the vascular endothelial barrier protective agent Y-27632 is opposite. The Y-27632 is a Rho kinase inhibitor and a cytoskeletal relaxant, affects cortical myosin activity and decreases actin-myosin activity, and has the functions of reducing the cell traction force and maintaining the permeability. The results of the two reagents measured by the double resonator QCM technology are consistent with their functions and the results of cell traction force measurement reported in the literature.

Figure 10:
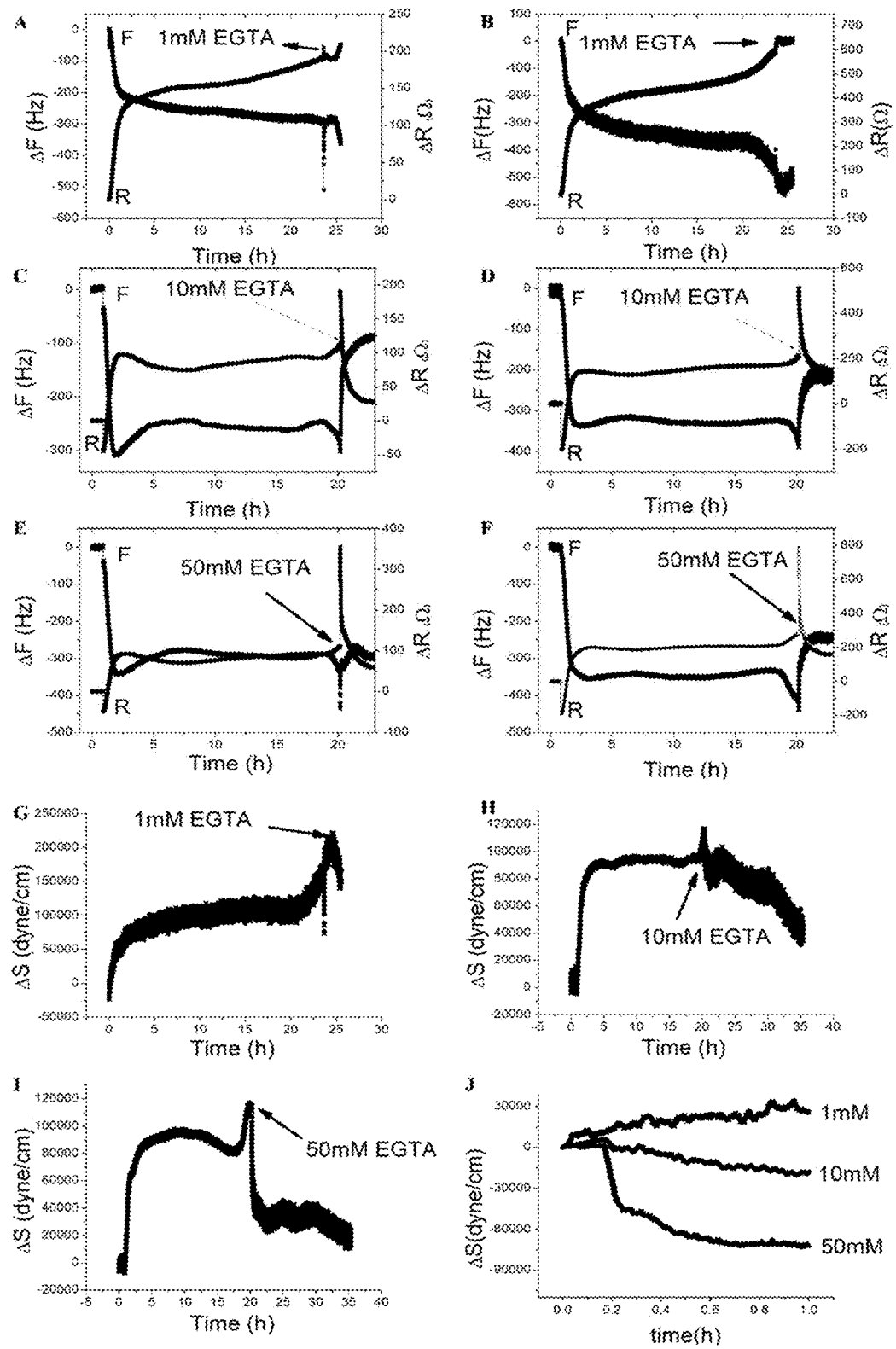
FIG. 10: example: dynamic QCM adhesion and force response curves under adhesion of 50,000 human umbilical vein endothelial cells to AT-cut and BT-cut bare gold electrodes, and under the action of EGTA of different concentrations (the final concentration added at the second arrow). (A) Frequency shift and dynamic resistance change curve under adhesion and 1 mM EGTA action, AT-cut; (B) Frequency shift and dynamic resistance change curve under adhesion and 1 mM EGTA action, BT-cut; (C) Frequency shift and dynamic resistance change curve under adhesion and 10 mM EGTA action, AT-cut; (D) Frequency shift and dynamic resistance change curve under adhesion and 10 mM EGTA action, BT-cut; (E) Frequency shift and dynamic resistance change curve under adhesion and 50 mM EGTA action, AT-cut; (F) Frequency shift and dynamic resistance change curve under adhesion and 50 mM EGTA action, BT-cut; (G) Dynamic cell traction force change curve under adhesion and 1 mM EGTA action; (H) Dynamic cell traction force change curve under adhesion and 10 mM EGTA action; (I) Dynamic cell traction force change curve under adhesion and 50 mM EGTA action; (J) Dynamic cell traction force change curve comparison under different EGTA concentrations.

Effects of EGTA of Different Concentrations on Traction Force of Human Umbilical Vein Endothelial Cells FIG. 10 shows the dynamic QCM responses during adhesions of 50,000 human umbilical vein endothelial cells to bare gold 9 MHz AT-cut and BT-cut quartz crystals and the subsequent actions of different EGTA concentrations. It can be seen that after 50,000 HUVECs are added, the QCM frequency decreases and the resistance increases. After 24 hours, the QCM frequency decreases by 300 to 400 Hz. In all experiments, except for the initial phase, the frequency shift of the BT-cut crystal is always greater than the frequency shift of the paired AT-cut crystal at the same time, so the surface stress ΔS applied to the electrode by cells in the adhesion process is positive. As the cells are spread, ΔS increases rapidly and then becomes stable. After 24 hours, ΔS reaches 115,000 to 175,000 dyne/cm (FIGS. 8G-I). After different concentrations of EGTA are added, the overall cell traction force shows a tendency to decrease, indicating that the cells are desorbing at this time. The cell morphology simulation experiments show that the cell spreading area observed became smaller after the EGTA treatments for five minutes, and the cells were retracted into ellipses. With the increase of EGTA time, except for the low 1 mM EGTA concentration, the cell generated force decreases, and decreases more quickly at 50 mM EGTA concentration than 10 mM EGTA concentration. This is consistent with the result of cell morphology simulation showing that the cell adhesion area is reduced more quickly with the increase of the EGTA concentration. Under the action of the low 1 mM EGTA concentration, the cell traction force in the initial phase did not decrease but increase slightly, and then the decreasing trend became consistent with those of the other EGTA concentrations tested. The integrins for cell-matrix interactions and the E-cadherins for cell-cell interactions are closely related to $Ca^{2+}$ concentrations. It is therefore expected that the EGTA chelated with $Ca^{2+}$ affects the dynamic adhesion and force balance of cell-matrix and cell-cell. Under 50000 endothelial cells, the short intercellular distance causes strong intercellular force. Therefore, we speculated that at the low 1 mM EGTA concentration, the EGTA acts mainly between cells, initially causing a decrease in cell-cell interaction, which in turn leads to an increase in cell traction force between cells and sensor matrices, and then a decrease in cell traction force between cells and the substrate.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A real-time and quantitative measurement method for cell traction force, comprising the following steps:
   (1) placing an AT-cut quartz crystal and a BT-cut quartz crystal in culture dishes or detection cells, wherein the AT-cut quartz crystal having the same frequency, surface morphology and/or modified surface adhesion molecules as those of the BT-cut quartz crystal; and
   (2) adding cells to be tested to the culture dishes or the detection cells, and measuring the cell traction force $\Delta S_t$ of the cells at an adhesion time t by the following formula:

$$\Delta S_t = (K_{AT} - K_{BT})^{-1}[t_q^{AT}\Delta f_t^{AT}/fr^{AT} - t_q^{BT}\Delta f_t^{BT}/fr^{BT}] \qquad (1),$$

wherein $K_{AT} = 2.75 \times 10^{-12}$ $cm^2$ $dyn^{-1}$ and $K_{BT} = -2.65 \times 10^{-12}$ $cm^2$ $dyn^{-1}$ are stress coefficients of the AT-cut quartz crystal and the BT-cut quartz crystal respectively; $fr^{AT}$ is the resonant frequency of the AT-cut quartz crystal, $fr^{BT}$ is the resonant frequency of the BT-cut quartz crystal, $tq^{AT}$ is the thickness of the AT-cut quartz crystal, $tq^{BT}$ is the thickness of the BT-cut quartz crystal, and all of which are constants; $\Delta f_t^{AT}$ and $\Delta f_t^{BT}$ are the frequency shifts of the AT-cut and BT-cut quartz crystals at any time t relative to their reference points respectively;
   when $\Delta S_t$ is negative, it indicates that the stress on the cells is a compressive stress, the cells are contracted, and the corresponding extracellular matrices are subjected to a tensile stress equal and opposite to the compressive stress; when $\Delta S_t$ is positive, the stress on the cells is a tensile stress, the cells are spread, and the corresponding extracellular matrices are subjected to a compressive stress equal and opposite to the tensile stress.

2. The method according to claim 1, wherein the cell adhesion molecules comprise extracellular matrix molecules capable of interacting with transmembrane proteins and integrins; extracellular matrix biomimetic molecules capable of interacting with transmembrane proteins and integrins; molecules capable of interacting with cell surface receptors; and molecules interacting with the surface of cells to promote cell adhesion.

3. The method according to claim 2, wherein the extracellular matrix molecules capable of interacting with transmembrane proteins and integrins are fibronectin, laminin, vitronectin or collagen; the extracellular matrix biomimetic molecules capable of interacting with transmembrane proteins and integrins are RGD adhesion sequence polypeptides; the molecules capable of interacting with cell surface receptors are molecules capable of interacting with cell surface cadherin; and the molecules interacting with the surface of cells to promote cell adhesion are poly-l-lysine.

4. The method according to claim 1, wherein in the formula of step (2), $t_q^{AT}=0.1661/fr^{AT}$; and $t_q^{BT}=0.2536/f_r^{BT}$.

* * * * *